(12) United States Patent
Daito et al.

(10) Patent No.: US 8,406,501 B2
(45) Date of Patent: Mar. 26, 2013

(54) METHOD AND SYSTEM FOR INSPECTION OF TUBE WIDTH OF HEAT EXCHANGER

(75) Inventors: Akihiro Daito, Handa (JP); Kaoru Okazoe, Anjo (JP); Atsushi Fukumoto, Nishio (JP); Tomoaki Yoshimori, Okazaki (JP)

(73) Assignee: Denso Corporation, Kariya (JP)

( * ) Notice: Subject to any disclaimer, the term of this patent is extended or adjusted under 35 U.S.C. 154(b) by 864 days.

(21) Appl. No.: 12/457,842

(22) Filed: Jun. 23, 2009

(65) Prior Publication Data

US 2010/0027872 A1 Feb. 4, 2010

(30) Foreign Application Priority Data

Aug. 1, 2008 (JP) ................................. 2008-200064

(51) Int. Cl.
*G06K 9/00* (2006.01)
*G09G 5/00* (2006.01)
(52) U.S. Cl. ........................ 382/141; 382/149; 345/619
(58) Field of Classification Search ........................ None
See application file for complete search history.

(56) References Cited

U.S. PATENT DOCUMENTS

| 7,260,250 B2 * | 8/2007 | Summers et al. ............. 382/128 |
| 2003/0011622 A1 * | 1/2003 | Yomdin et al. ................. 345/630 |
| 2005/0226494 A1 * | 10/2005 | Yamamoto et al. ........... 382/149 |
| 2007/0019856 A1 * | 1/2007 | Furman et al. ................ 382/141 |

FOREIGN PATENT DOCUMENTS

| JP | 2002250611 A | * | 9/2002 |
| JP | A-2005-321300 | | 11/2005 |

\* cited by examiner

*Primary Examiner* — Ryan Zeender
*Assistant Examiner* — Dana Amsdell
(74) *Attorney, Agent, or Firm* — Oliff & Berridge, PLC (57) ABSTRACT

A method and system for appearance inspection of a core of a heat exchanger provided with fins and tubes, performing averaging and dynamic binarization on the imaging data to extract an image of only a tube, then calculating, with respect to the extracted tube image, a center axis across a long direction of the tube comprised of the center coordinates of the tube width direction, comparing the discovered center axis with a reference value to find the maximum displacement across the long direction of the tube, and judging the tube is a defect when the maximum displacement is greater than a predetermined threshold.

5 Claims, 8 Drawing Sheets

METHOD AND SYSTEM FOR INSPECTION OF TUBE WIDTH OF HEAT EXCHANGER

BACKGROUND OF THE INVENTION

1. Field of the Invention

The present invention relates to an appearance inspection method and system of a heat exchanger, more particularly relates to an appearance inspection method and system of a fin-and-tube type heat exchanger used in automotive heaters and the like.

2. Description of the Related Art

Figure 1:
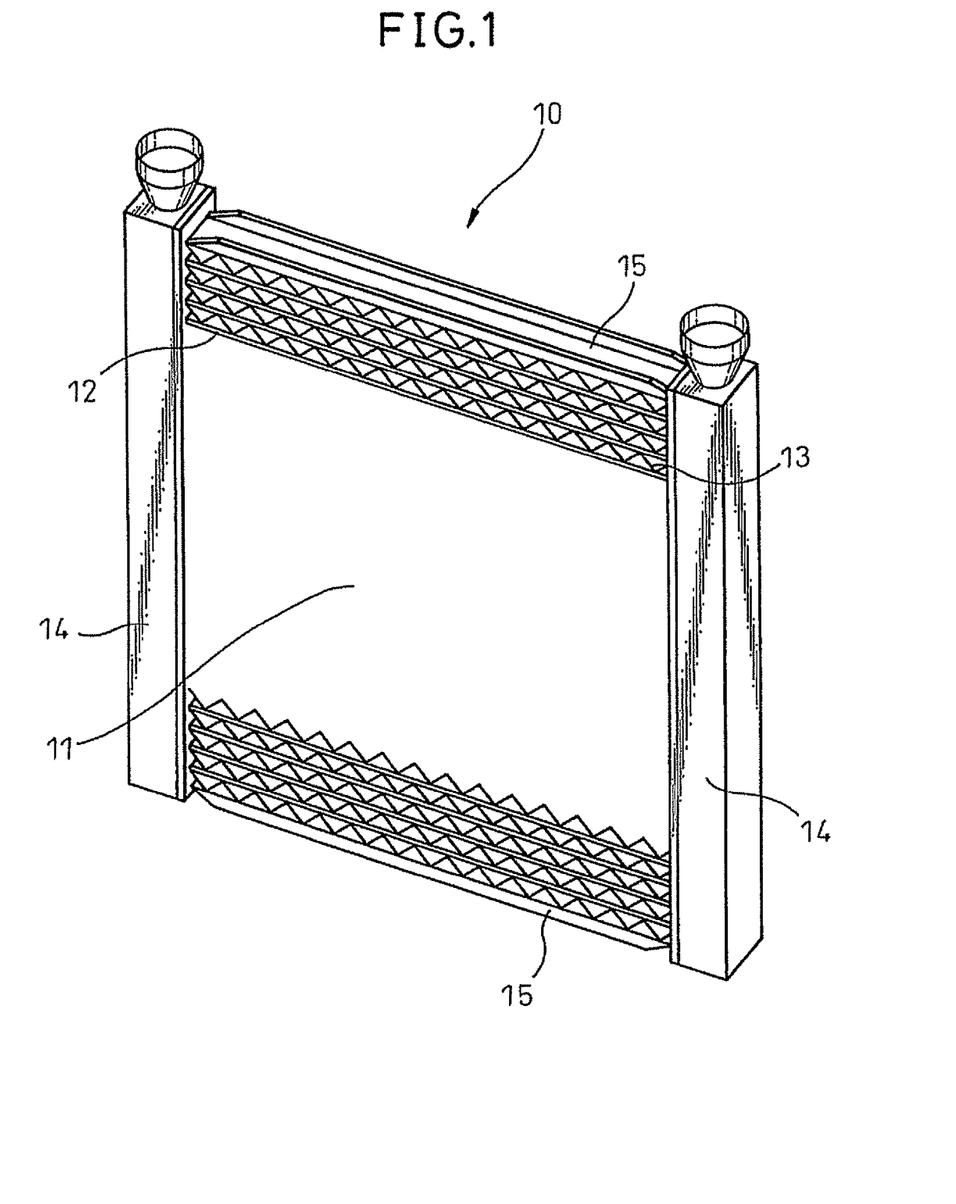
Figure 2:
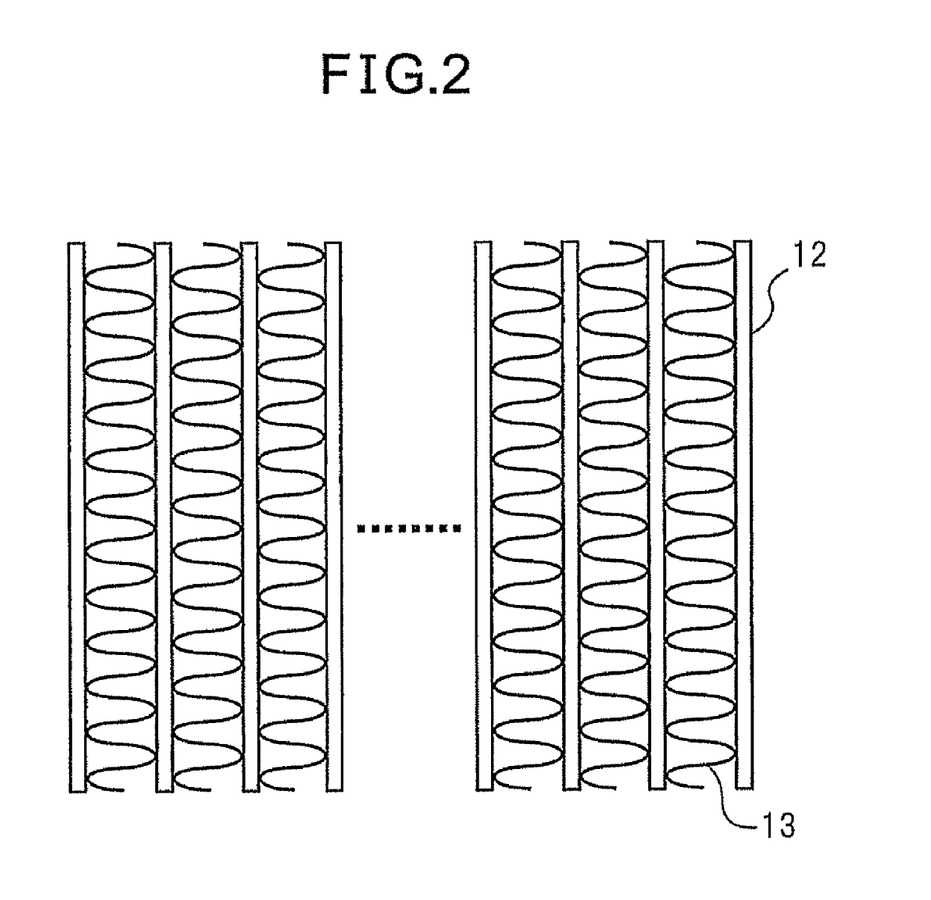
FIG. 2 is a view rotating the heat exchanger 10 of FIG. 1 by 90 degrees and showing the fin and tube part enlarged.

FIG. 1 is a perspective view showing a fin-and-tube type heat exchanger 10 generally used in automotive heaters and the like. FIG. 2 is an enlarged view of the fin and tube parts wherein the heat exchanger 10 of FIG. 1 is rotated 90 degrees. The heat exchanger 10 is provided with a core 11 serving as a heat exchanger part. The core 11 is provided with a plurality of tubes 12 through which a fluid serving as a heat exchange medium passes and a large number of fins 13 that are attached to the surfaces of the tubes to increase the heat transfer area. Reference numerals 14 indicate tank parts and 15 side plates.

The core 11 of the fin-and-tube type heat exchanger 10 is formed by a plurality of unit elements, each provided with one straight tube 12 and a fin 13 attached in a bellows-like state on its surface, regularly repeated and connected. In such a unit element, the fin 13 is comprised of a flat sheet folded into an S-shape which is repeated to form a bellows shape. The fin 13 is therefore a folded part provided with a plurality of curved parts (fin R parts). Defects in the tubes 12 and fins 13 of such a heat exchanger can be detected by appearance inspection with a considerable success rate. Such appearance inspection has been improved for automation, labor-saving, and raising accuracy up to now. Recently, inspection methods making use of image processing have been introduced.

As such an inspection method using image processing, the inspection method such as shown in Japanese Unexamined Patent Publication (A) No. 2005-321300 is known.

This inspection method is an appearance inspection method of a core of a heat exchanger having a repeated pattern of the two components of a tube and fin. According to this inspection method, two images are captured in order to apply a fault detection method using image processing. One of the images of the part being inspected is an image captured as a tube inspection image while controlling the illumination so that the brightness of the image of the fin part is suppressed. The other inspection image is captured as a fin inspection image by an illumination by which the fin part can be inspected.

Further, a two-dimensional Fourier transform is applied to these tube or fin inspection images to obtain inspection images at the spatial frequency domains. Next, for example, parts of the input images are utilized to prepare mask image data for samples of good parts and this data is used to remove the frequency components of the good parts from the inspection images. Then, a two-dimensional inverse Fourier transform is further applied to obtain fault detection images.

However, when using the aforementioned prior art for inspecting tubes, the following problems have occurred. That is, in order to extract a tube, it was necessary to capture two inspection images at illuminations suitable for the tubes or the fins. When obtaining a tube inspection image, the image is captured while adjusting the level of the brightness until the fins are no longer visible, so differences in the surface conditions of a workpiece have become a cause of detection errors in inspection.

In tube inspection, transformed images of the inspection images obtained by application of a fast Fourier transform (FFT) and the transformed images of a normal tube part of the inspection image are used to find defects, so unless all of the tubes are at equal pitches, good precision detection is not possible. Further, by applying an FFT to the entire core, factors leading to detection errors will occur and the amount of data will end up becoming massive. In the case of FFT analysis, the transforms have to be applied twice, for regular and inverse, or else defects cannot be detected, thus causing the processing speed to drop. When performing inspection processing using FFT analysis, judgment based on the dimensional threshold value was difficult.

Figure 3:
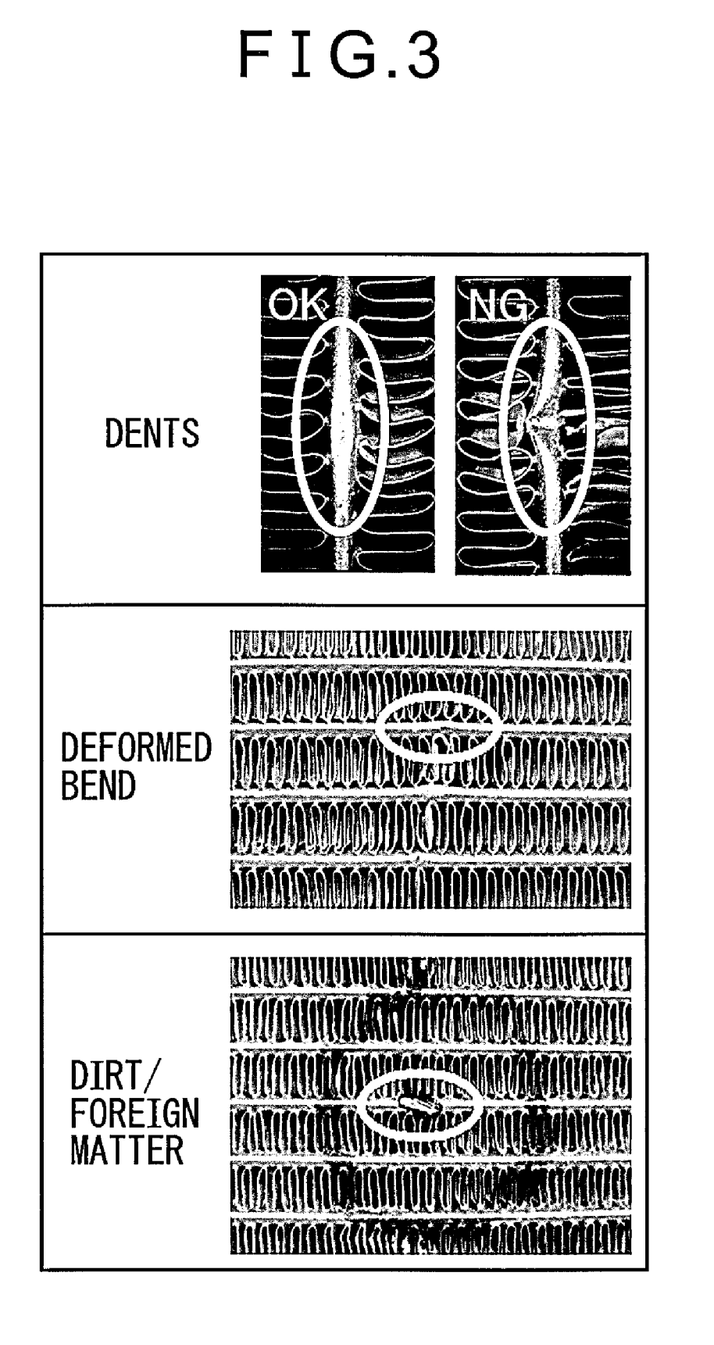
FIG. 3 is a view showing examples of tube defects.

FIG. 3 is a view showing examples of tube defects.

As modes of defects of the tubes, there are dents, deformed bends, deposits of dirt/foreign matter, etc. A "dent" is a defect resulting from a tube being struck and indented. As examples of the dents, there are cases where the indented part is sharp in angle and the width center of a tube is greatly indented. A dent where the center of a tube is greatly indented is displayed on the image as a black mark. A "deformed bend" is a defect in which the tube width greatly changes due to a deformed bend. A "deposit of dirt/foreign matter" on a tube is a dirt/foreign matter deposit defect and is displayed on the image as a black mark. Up until now, these defects could not be identified.

SUMMARY OF THE INVENTION

To solve the aforementioned problems, the invention in claim 1 is an appearance inspection method of a core of a heat exchanger provided with fins and tubes, comprising a step of having an imaging device capture an image of the core and inputting into an image processing device the image data for storage, a step of identifying a region in the image data in which an image of a single tube is captured, a step of performing averaging and dynamic binarization of the image data in this region to extract only the image of the tube, a step of finding the smallest rectangle surrounding a tube for the image of the tube extracted so as to find a width dimension and length dimension of the tube, a step of comparing the tube width dimension and length dimension found respectively with a predetermined width threshold value and a predetermined length threshold value to judge tube quality, a step of finding, with respect to the extracted tube image, a center axis across a long direction of the tube formed from center coordinates of the width direction of the tube, and a step of comparing the found center axis with a reference value to find a maximum displacement of the center axis across the long direction of the tube and judging the tube is defective when the maximum displacement is a predetermined threshold or more.

Due to this, modes of tube defects can be identified with greater accuracy and it is possible to increase the processing speed.

The invention in claim 2 is an appearance inspection system of a core of a heat exchanger provided with fins and tubes, the appearance inspection system being provided with an imaging device and an image processing device, and the image processing device comprising a storage means for inputting and storing image data of the core captured by the imaging device, an image processing means for identifying a region in the image data in which the image of a single tube is captured, performing averaging and dynamic binarization on the image data in this region to extract only an image of a tube, a calculating means for finding, with respect to the extracted tube image, the center axis across the long direction of the tube comprised of the center coordinates of the width direction of the tube, and a judging means for comparing the center axis found with a reference value to find a maximum displacement of the center axis across the long direction of the tube and judging that the tube is a defect when the maximum displacement is a predetermined threshold or more.

Thereby, in the same way as the invention of claim 1, modes of tube defects can be identified with greater accuracy and it is possible to increase the processing speed.

BRIEF DESCRIPTION OF THE DRAWINGS

These and other objects and features of the present invention will become clearer from the following description of the preferred embodiments given with reference to the attached drawings, wherein:

FIG. 1 is a perspective view showing a fin-and-tube type heat exchanger 10 generally used in an automotive heater and the like;

DESCRIPTION OF THE PREFERRED EMBODIMENTS

Figure 4:
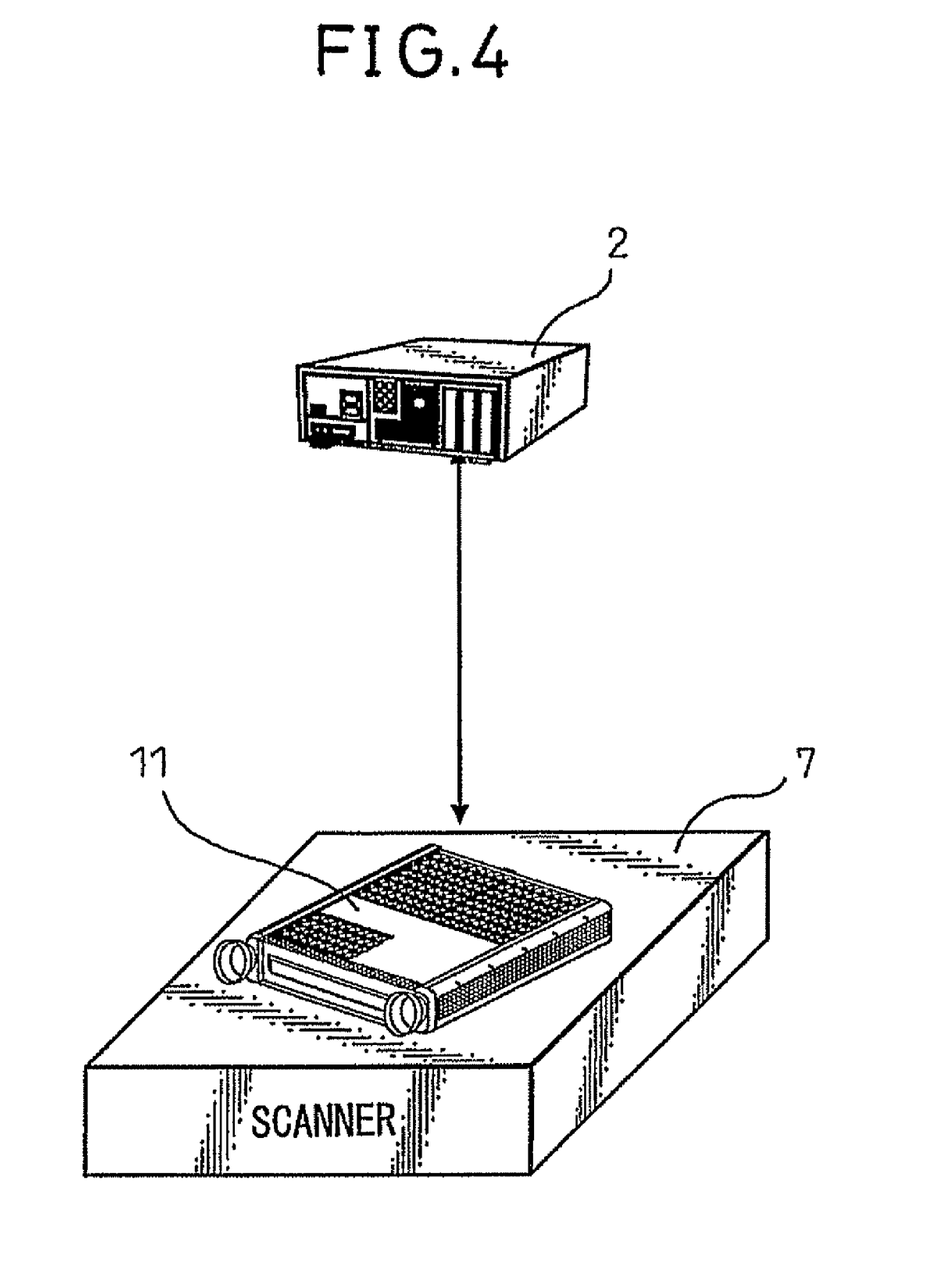
FIG. 4 is a schematic view of a tube width inspection system using a scanner.
Figure 5:
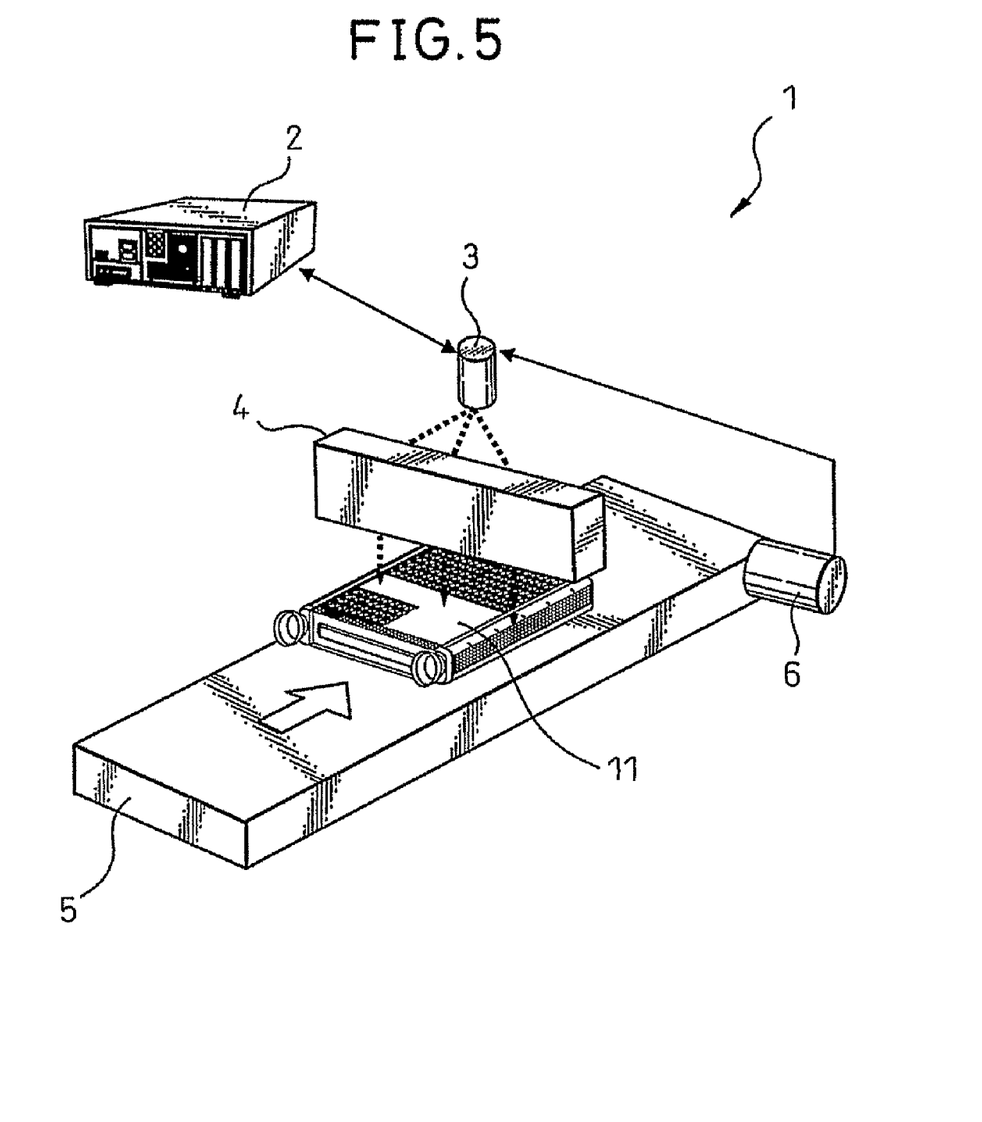
FIG. 5 is a schematic view of a tube width inspection system using a belt conveyor.

FIG. 4 is a schematic view of the hardware of a tube width inspection system using a scanner, while FIG. 5 is a schematic view of the hardware of a tube width inspection system using a belt conveyor.

Below, referring to FIG. 5, one embodiment of the present invention concerning a tube width inspection system using a belt conveyor will be explained.

In the following embodiment, the object of inspection is the core 11 of a fin-and-tube type heat exchanger 10 used in automotive heaters and the like. Each component element of the fin-and-tube type heat exchanger being inspected is designated by the same notation as in FIG. 1.

The inspection system 1 shows an inspection system for inspecting a top surface of the core of the fin-and-tube type heat exchanger 10. In the inspection of the bottom surface of the core as well, an inspection system 1 having a similar configuration is used to perform inspection using a similar operation. The inspection system 1 is provided with an image processing device 2, a CCD camera or other imaging device 3, a focusing (lens)/illumination device 4, a belt conveyor 5, and an encoder 6 (not necessarily required) coupled to a drive unit of the belt conveyor.

In response to a signal from the encoder 6, the focusing/illumination device 4 illuminates the core 11 of the heat exchanger being inspected, the imaging device 3 captures an image of the tubes and the fins of the core part, and sends image data to the image processing device 2. The image processing device 2 converts this from an analog to digital format, then converts the image to 256 tone image data, and stores it as raw image data in a storage means.

In a tube width inspection system using a scanner 7 shown in FIG. 4 as well, the following processing is similar to that of the tube width inspection system using a belt conveyor of FIG. 5.

A variety of possible means may be considered for selecting a single tube for judgment from the raw image data. To set the range of processing for the raw image data, first it is necessary to determine a reference point and set a first window with respect to the raw image data. In the first window, the reference point is determined while setting the long direction of the tube as the Y-axis. As the method of determining the reference point, as one example, it is possible to set the reference point by having the core 11 conveyed on a belt conveyor along a conveyor guide, having the imaging device 3 detect the tip of the core 11, and using already input product dimension data. Also, it is possible to set the reference point by processing the image and finding the overall external shape.

The center reference position for each tube can be found from the product dimension data or by image processing, so a single tube for judgment is selected from among these. Using the aforementioned center position as a reference, a rectangular second window W is set in a perpendicular direction (X-axis) to the long direction of the tube (Y-axis) using an X-axis length adding a constant value to the tube width of the product dimension data and a Y-axis length adding a different constant value to the tube length. The Y-axis direction of the second window W is also the long direction of the tube. The aforementioned constant values are values empirically determined when judging tube defects.

Before starting selection of a single tube, a process of removing defects in advance other than tube defects is necessary. To accomplish this, a process of inspecting for the presence of remaining wire mentioned later may be provided.

The second window W is divided into small regions. For each small region, averaging is performed on the raw image data. The result is referred to as an "averaged image", in which only fin image remains. For example, if the tube width is 10 pixels, an aforementioned small region having 30 pixels in an X-axis direction and 1 pixel in a Y-axis direction may be mentioned. The image processing means performs dynamic binarization to obtain the difference between the brightness of the aforementioned averaged image and the brightness of the raw image. As a result, an image of only the tube is extracted from the raw image.

In the following explanation, the tube is extracted as a white luminance, and the parts other than the tube are extracted as black luminance. In order to remove noise, opening processing is performed.

In this second window W, the tube is surrounded by a rectangle, the sides of the rectangle are shortened until any point of the tube contacts the rectangle, the sides of the rectangle at that time are found (called smallest rectangle surrounding tube), and the X-axis direction width t and the Y-axis direction length l are calculated.

This processing is successively repeated in the first window based on the product dimension data etc. to select the single tubes and extract images of all of the tubes.

Figure 6A:
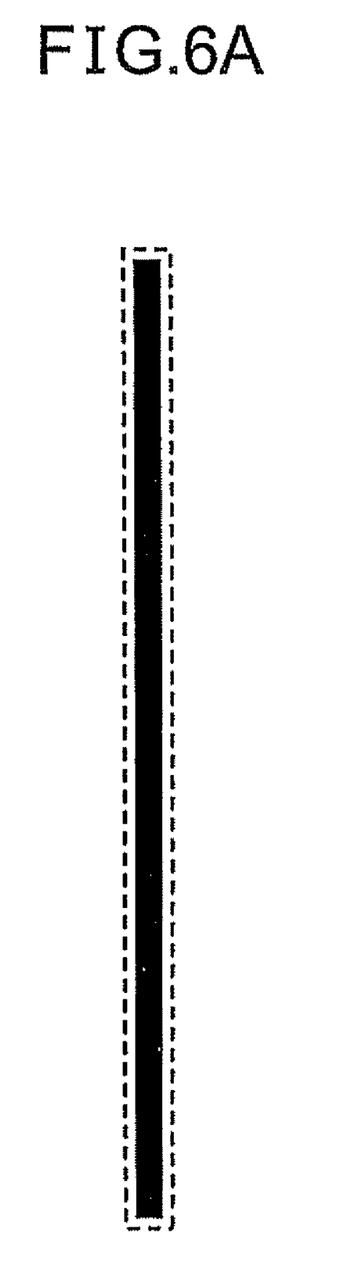
FIG. 6A is an explanatory view of a case when inspecting a normal straight tube.
Figure 6B:
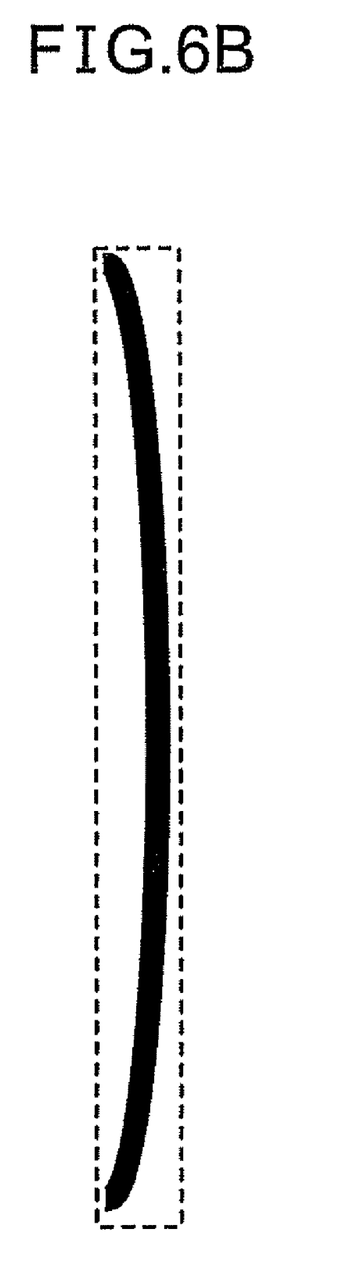
FIG. 6B is an explanatory view of a case when inspecting a tube bent into a bow shape.

In the case of surrounding a tube by a smallest rectangle for inspection, FIG. 6A is an explanatory view of inspection in a normal case and FIG. 6B is an explanatory view of inspection in a case in which the tube is bent. For each single tube, the smallest rectangle surrounding the tube is found and the obtained X-axis direction width t and Y-axis direction length l are respectively compared with a predetermined value a1 of the width and a predetermined value b1 of the length.

Figure 8:
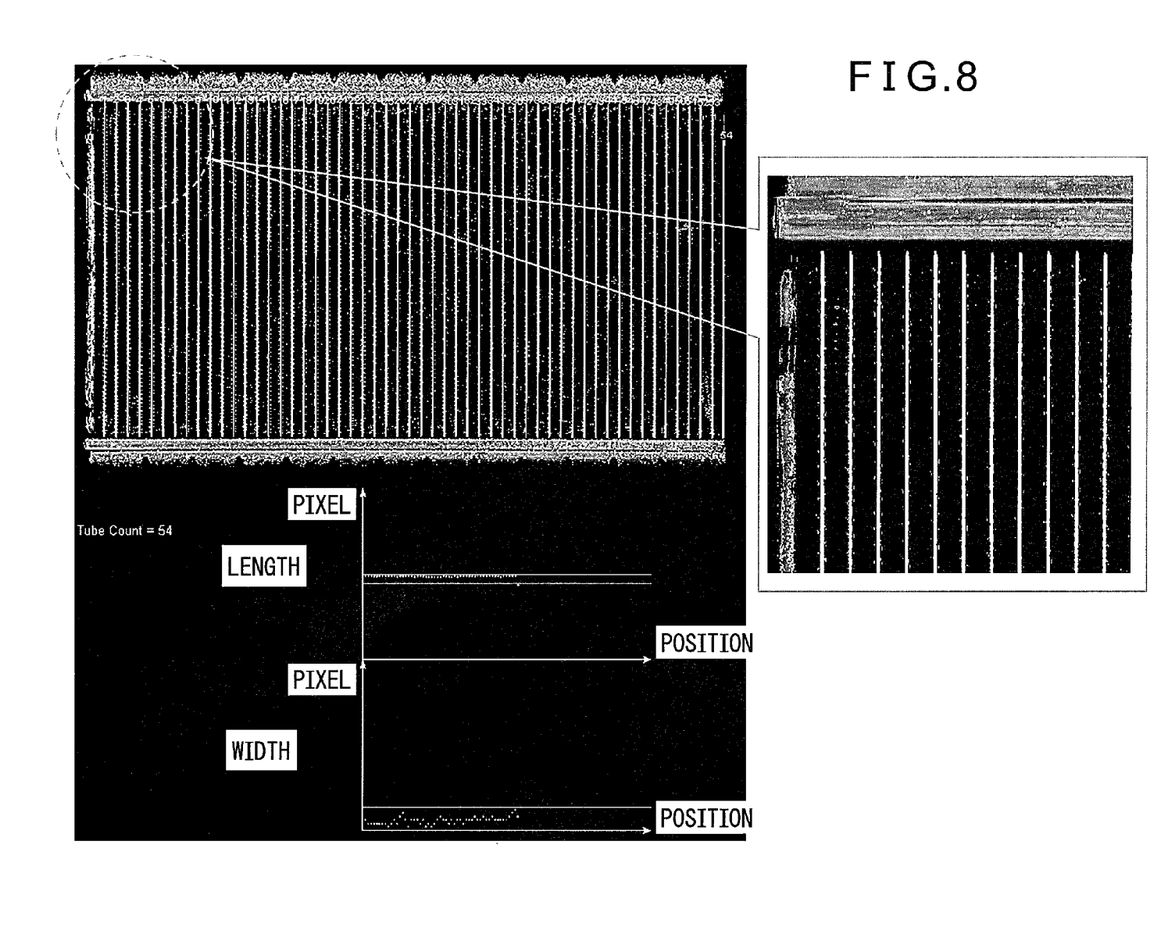
FIG. 8 is an example showing parts of tube inspection.

The predetermined value a1 of the width and the predetermined value b1 of the length may be empirically determined within an allowable range as a good part. FIG. 8 is an example showing parts of tube inspection.

The tube length l is compared with the predetermined value b1 of the length. If it is smaller, it is judged that there is an anomaly in the tube length or the tube end part, and that it is a defect. If b1 or more, the tubes are all judged to be good.

The tube ends are inserted in the tank part, however, a tube can be separated by image processing in the following manner. There is a difference in level between the tank top surface and the tube top surface (the "tube top surface" refers to the surface of the tube 12 at the upward side of the page of FIG. 2. The same applies to the "tank top surface"). Due to this level difference, a shadow can form on a tube, so it is possible to separate it in the image.

Once the comparison between the tube length l and the predetermined value b1 is completed, next, the judgment of the tube width t is started. It is compared with the predetermined value a1 of the width. If it is larger, it is judged that there is an anomaly in the tube shape and that it is a defect. The predetermined value a1 is set to be somewhat larger than the normal tube width, that is, a value by which it is deemed that the limit as a good part has clearly been exceeded. If all the a1 or less, the next judgment process is started.

Next, tube skeleton is detected. This processing is one of the characterizing portions of the present invention. Due to this, tube defects can be more precisely detected and types of tube defects can be judged to a certain degree.

"Tube skeleton detection" is basically the calculation of the center axis of the tube. The positional coordinates of the tube center point in the X-axis direction are successively calculated for each small value $\Delta\alpha$ along the Y-axis for all extracted single tubes. What connects these center points along the Y-axis is the center axis of the tube. At the same time, the difference value $\Delta t$ of the positional coordinates of the two ends of the tube on the X-axis is calculated for each small value $\Delta\alpha$ along the Y-axis.

First, the technical significance of the "difference value $\Delta t$" of the positional coordinates of the two ends of the tube on the X-axis direction will be explained. This value shows the change in the tube width along the Y-axis of the tube width. A defect in which the center of a tube is greatly indented is displayed on the image as a black mark. A defect in which dirt/foreign matter is deposited on the tube is a dirt/foreign matter deposit defect and is shown on the image as a black mark. In these cases, breaks in the tube occur frequently. These breaks are expressed as zero values in the difference value $\Delta t$.

Accordingly, if this difference value $\Delta t$ is a value of the small value $\epsilon 1$ close to zero or less, a break will occur in the image. In this case, this is differentiated as a tube defect of a defect in which the center of a tube is greatly indented or a dirt/foreign matter deposit defect.

Next, the technical significance of the "tube center axis" will be explained.

In general, when binarizing tubes to extract only the tubes, noise such as the fins will remain. Therefore it is necessary to remove the noise when judging whether the tube is good or a defect by the tube width. At both sides of the tube, there are curved parts of the fins (fin R parts). If there is flux residue at these parts, no matter how thin the fins, noise cannot be eliminated. This noise will remain at the tube, whereby the tube will end up being judged as thick.

By finding the tube center axis, the influence of the noise can be reduced and noise can be removed in instances when the same type of noise appears at the two sides simultaneously.

As opposed to this, as seen in the dent in FIG. 3, in a tube defect in which the indented part is sharp in angle, both sides of the tube displace, thus causing a large displacement in the center axis.

A calculating means of displacement $\Delta T$ of the center axis of the tube is illustrated below. As one example, the center coordinates for the positional coordinates of the two sides of a tube are successively found along the Y-axis direction and used as the center axis. A means of finding the difference of the maximum value and the minimum value of the displacement of this center axis and comparing it to a predetermined threshold is possible. In this case, noise will have an effect.

With respect to the aforementioned center axis, it is possible to find a reference value (straight line) by the least square method or draw a straight line so that the fluctuation of the center axis in the X-axis direction becomes zero by an integrated average and use this as the reference value. This may be found by the means of obtaining the difference between the maximum value (or the minimum value) of the displacement of the aforementioned center axis and their reference values and comparing this with a predetermined threshold. The reference value may also be found by other known processing. The reference value of the displacement of the center axis does not have to be a straight line and may be a curve.

The aforementioned predetermined threshold may be empirically determined within an allowable range of good parts while taking into consideration the influence of the fins and tube bents. Further, the reference value was calculated in the process of finding the aforementioned enter axis of the tube, but it is also possible to use this reference value, find the pitch of the tubes, and compare the pitch with a predetermined value to judge tube defects.

The displacement $\Delta T$ of the tube center axis is compared with a predetermined value c1. If this predetermined value c1 or less, the judging means judges the tube to be good, while if greater than this, the judging means judges the tube as being a dented with an indented part of a sharp angle or otherwise defective. Further, a different predetermined value c2 greater than the predetermined value c1 may be provided to identify deformed bends and dents with sharp indented parts.

To inspect for tube defects, a process removing defects in advance other than tube defects is necessary. Here, a process for inspecting for the presence of remaining wire will be explained.

In order to keep the tubes, fins, and other parts from falling apart during transport after assembly of the core until the core is heat treated, a wire is wrapped around the center part of the core. After heat treatment for brazing, that wire is no longer necessary and thus is cut off, however, there are cases where the wire sticks to the core due to the attachment of the wire to the core surface and therefore the wire cannot be removed. In this case, identification of each single tube in image processing is not possible, so this process is necessary before proceeding with tube inspection.

The process for inspecting for the presence of remaining wire is as follows.

Remaining wire has the property of occurring at the center part of the entire core (the wire is only wound around the center part of the core), so the area of the center of the wire winding part is made the region where the number of tubes is counted. If the count is the number of tubes according to the product data, no wire remains. Further, if the count is different from the number of tubes, there is wire remaining.

Figure 7:
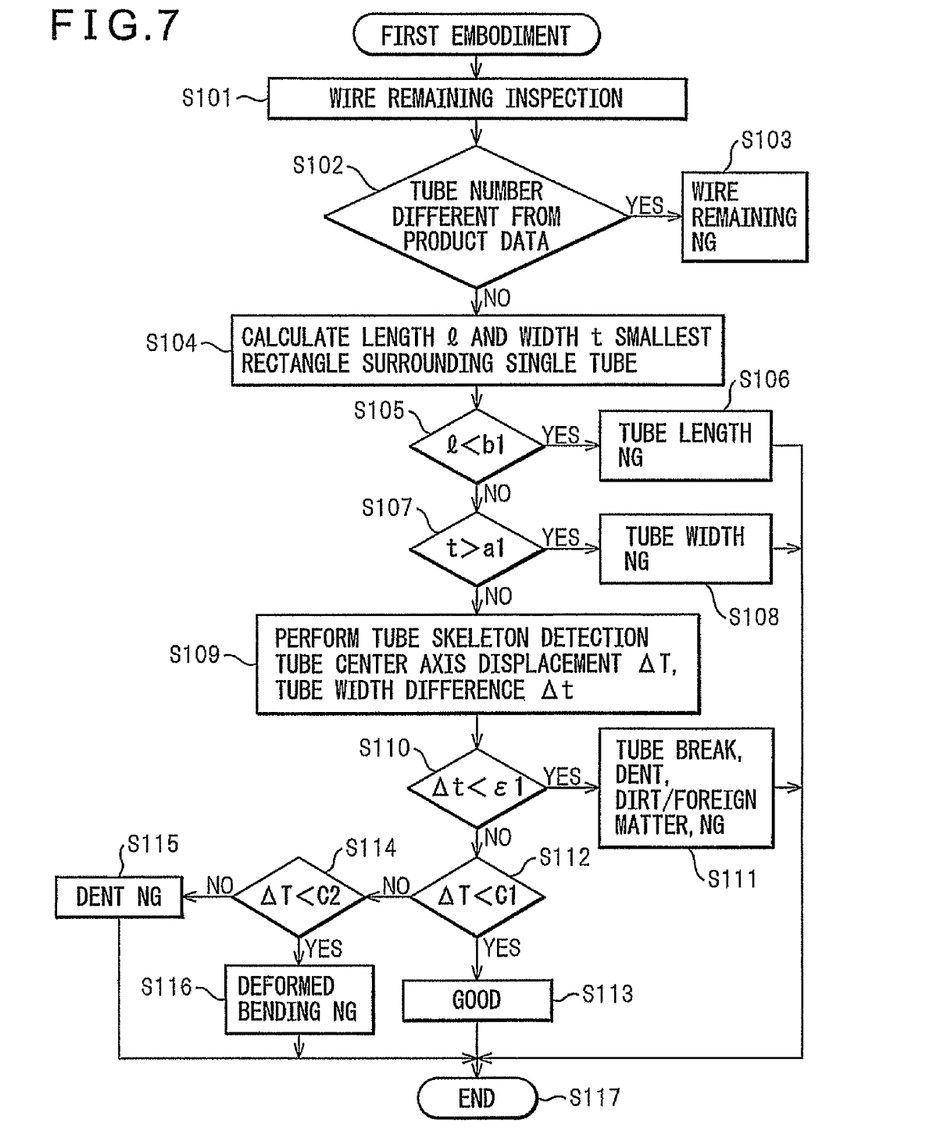
FIG. 7 is a schematic view of a flow chart for an embodiment of the present invention.

FIG. 7 is a schematic view of a flow chart for a first embodiment of the present invention. The aforementioned tube defects will be explained following the schematic view of the flow chart of FIG. 7.

At step S101, processing for inspection for remaining wire is performed. At step S102, it is judged whether the number of tubes obtained from image processing is different from the number according to the product data (product serial number information). If YES, the routine proceeds to step S103 where processing for remaining wire defect is performed. If NO at step S102, then as mentioned above, the routine proceeds to step S104 where the smallest rectangle surrounding a single tube is found to calculate the length l and the width t. At step S105, if the length l is less than a predetermined value b1, the routine proceeds to step S106 where processing for dealing with abnormalities in the tube length is performed. If NO at step S105, the routine proceeds to step S107. If the width t is greater than a predetermined value a1, the routine proceeds to step S108 where processing for dealing with abnormalities in the tube width is performed.

If NO at step S107, the routine proceeds to step S109 where tube skeleton detection processing is performed and the tube center axis displacement ΔT and tube width difference Δt are obtained. At step S110, if Δt is smaller in comparison with the small value ε1, the routine proceeds to step S111 where processing of defects such as dents (tube center indented) and dirt/foreign matter is performed. If NO at step S110, the routine proceeds to step S112 where the tube center axis displacement ΔT is compared with the predetermined value c1. If ΔT is greater than c1, at step S114, the tube center axis displacement ΔT is compared with the predetermined value c2. If Δt is smaller than c2, at step S116, processing is performed for a deformed bend defect. If NO at step S114, the routine proceeds to step S115 where processing is performed for a dent defect. If YES at step S112, the tube is judged good and the processing is ended. The processing from step 104 to step 117 is repeated for all single tubes of the core.

The defect processing of steps S103, S106, S108, S111, S115, and S116 may be determined according to the respective characteristics. The same defect processing may be performed for these steps. Further, it is acceptable, depending on the accuracy of the defect judgment, for some tubes to be automatically treated as defective and the rest to be visually inspected then subjected to a manual selection process and repair process.

As another embodiment, at the aforementioned step S108, it is also possible to perform processing in which a tube can be judged as good when it is slightly bent into a bow shape. This processing divides the second window W into a whole number n of blocks in the Y-axis direction and finds the smallest rectangle corresponding to each divided segment of the tube at each block to calculate the X-axis direction width. The measured $a_1, a_2, a_3, a_4, a_5$, etc. are compared with a threshold value A of a width where a tube bent into a bow shape can be judged to be good and, when all are below it, the tube is judged to be good.

The present invention was explained with regards to an automotive heater, however, it may be applied to inspection of general radiators as well.

As explained above, according to the present invention, it is possible to judge modes of tube defects and inspections with greater accuracy can be performed.

While the invention has been described with reference to specific embodiments chosen for purpose of illustration, it should be apparent that numerous modifications could be made thereto by those skilled in the art without departing from the basic concept and scope of the invention.

The invention claimed is:

1. An appearance inspection method of a core of a heat exchanger provided with fins and tubes, comprising:
   a step of having an image device capture an image of the core of the heat exchanger and inputting into an image processing device the image data for storage, the image processing device performing:
   a step of identifying a region in the image data in which an image of a single tube of the heat exchanger core is captured,
   a step of performing averaging and dynamic binarization of the image data in this region to identify and extract only the image of the tube,
   a step of finding the smallest rectangle surrounding a tube for the image of the tube extracted so as to find a width dimension and length dimension of the tube,
   a step of comparing the tube width dimension and length dimension with a predetermined width threshold value and a predetermined length threshold value, respectively, to judge tube quality,
   a step of finding, with respect to the extracted tube image, a center axis in the longitudinal direction of the tube formed from center coordinates of the width direction of the tube, and
   a step of comparing the found center axis with a reference value to find a maximum displacement of the center axis across the longitudinal direction of the tube and judging the tube is defective when the maximum displacement is a predetermined threshold or more.

2. An appearance inspection system of a core of a heat exchanger provided with fins and tubes,
   the appearance inspection system being provided with an imaging device and an image processing device, and
   the image processing device comprising
   a storage means for inputting and storing image data of the core of the heat exchanger captured by the imaging device,
   an image processing means for identifying a region in the image data in which the image of a single tube of the heat exchanger is captured and performing averaging and dynamic binarization on the image data in this region to extract only an image of a tube,
   a calculating means for finding, with respect to the extracted tube image, the center axis in the longitudinal direction of the tube comprised of the center coordinates of the width direction of the tube, and
   a judging means for comparing the center axis found with a reference value to find a maximum displacement of the center axis across the longitudinal direction of the tube and judging that the tube is a defect when the maximum displacement is a predetermined threshold or more.

3. The appearance inspection method of claim 1, further comprising:
   a step of finding the width of the tube at one or more locations in the longitudinal direction, formed from the positional coordinates of the ends of the tube in the width direction, and
   a step of judging the tube as having a defect when the width is less than a predetermined value.

4. The appearance inspection method of claim 1, further comprising:
   a step of comparing the found center axis with a reference value to find the pitch of the tube, and
   a step of judging the tube to be a defect by comparing the found pitch to a predetermined pitch value.

5. The appearance inspection method of claim 1, further comprising:
 a step of inspecting the core of the heat exchanger for the presence of remaining wire, comprising:
 a step of identifying a region of the core where the wire was wrapped,
 a step of counting the number of tubes of the heat exchanger in the identified region,
 a step of comparing the number of tubes counted with a predetermined number, and
 a step of judging that wire remains if the number of tubes counted does not equal the predetermined number.

* * * * *